United States Patent [19]

Ishihara et al.

[11] Patent Number: 5,000,880

[45] Date of Patent: Mar. 19, 1991

[54] NOVEL PROCESS FOR PRODUCING PHOSPHATIDYLCHOLINE DERIVATIVES

[75] Inventors: Masami Ishihara, Kawagoe; Hiroyoshi Nawa, Fujimi; Tsutomu Miyagawa, Kawagoe, all of Japan

[73] Assignee: Wako Pure Chemical Industries, Ltd., Tokyo, Japan

[21] Appl. No.: 359,914

[22] Filed: Jun. 1, 1989

[30] Foreign Application Priority Data

Jun. 2, 1988 [JP] Japan .................................. 63-136564

[51] Int. Cl.$^5$ ............................................... C07F 9/10
[52] U.S. Cl. ..................................................... 260/403
[58] Field of Search ......................................... 260/403

[56] References Cited

U.S. PATENT DOCUMENTS 4,130,571 12/1978 Nakajima et al. ................... 260/403
4,690,784 9/1987 Nanba et al. ........................ 260/403

OTHER PUBLICATIONS

Biochim. Biophys. Acta 187 (1969), 520–526.

Primary Examiner—Mukund J. Shah
Assistant Examiner—F. Bernhardt
Attorney, Agent, or Firm—Armstrong, Nikaido, Marmelstein, Kubovcik & Murray

[57] ABSTRACT

Glycero-phosphatidylcholine is acylated with a higher fatty acid anhydride in the presence of a special organic solvent in the absence of a catalyst.

5 Claims, No Drawings

NOVEL PROCESS FOR PRODUCING PHOSPHATIDYLCHOLINE DERIVATIVES

BACKGROUND OF THE INVENTION

This invention relates to a novel process for producing phosphatidylcholine derivatives useful as elementary material of liposomes, etc. used in the field of drug-delivery system (DDS) and clinical diagnostic drug.

As the method for producing diacyl-phosphatidyl-cholines (hereinafter simply referred to as "DAPC"), acylation of glycero-phosphatidylcholine is usually adopted and has been widely practised hitherto. This method can roughly be classified into the following four processes.

(1) Acylation using fatty acid chloride (Can. J. Biochem. Physiol., 37, 953 (1959), etc.);

(2) Acylation using 1-acylimidazole (U.S. Pat. No. 4,130,571);

(3) Acylation using fatty acid anhydride in the absence of solvent (Biochim. Biophys. Acta, 187, 520 (1969), etc.);

(4) Acylation using fatty acid anhydride in the presence of an esterification catalyst such as N,N-dimethyl-4-aminopyridine, N,N-pyrrolidinopyridine or the like (U.S. Pat. No. 4,690,784).

However, all these processes are disadvantageous in the following points. Thus, the acylation process (1) using fatty acid chloride is disadvantageous in that the reaction cannot progress sufficiently unless a basic catalyst such as pyridine and the like is used, and when such a basic catalyst is used the catalyst remaining in the system after the reaction must be removed by the use of ion exchange resin or the like, which makes the procedure troublesome. The acylation process (2) which comprises converting a fatty acid into imidazole derivative to activate the acyl group and then carrying out acylation with the derivative is disadvantageous in that the reaction takes a long period of time and gives only a low yield, the acylating agent liberates imidazole of which separation and removal is troublesome similarly to above, and the acylating agent is expensive. The acylation process (3) which comprises carrying out acylation in the absence of solvent by the use of a fatty acid anhydride is disadvantageous in that the reaction system has a high viscosity, workability of the process is not good, and the reaction takes a long period of time, so that the process is by no means adoptable commercially. The acylation process (4) which comprises carrying out acylation by the use of fatty acid anhydride in the presence of a basic catalyst is disadvantageous in that the basic catalyst remaining after the reaction must be removed with ion exchange resin or the like, which results in increasing the number of steps and makes the procedure troublesome.

SUMMARY OF THE INVENTION

An object of this invention is to provide an easily commercializable process for producing DAPC by which DAPC of high purity can be obtained in a high yield with good workability, without troublesome procedure, in a relatively short period of time.

This invention provides a process for producing a phosphatidylcholine derivative represented by the following general formula:

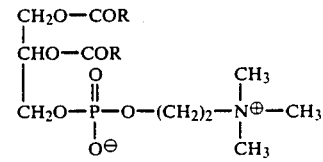

wherein R represents saturated or unsaturated, straight or branched chain hydrocarbon residue, which comprises supporting glycero-phosphatidylcholine (GPC) represented by the following formula:

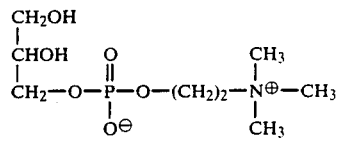

on a higher fatty acid metallic salt and acylating it with a higher fatty acid anhydride represented by the formula: $(RCO)_2O$ wherein R is as defined above, in the absence of catalyst and either (1) in an organic solvent having active hydrogen atom on carbon atom and free from the risk of undergoing acylation in itself or (2) in the presence of an organic solvent having active hydrogen atom on carbon atom and free from the risk of undergoing acylation in itself and another organic solvent not disturbing the acylation of glycero-phosphatidylcholine and free from the risk of undergoing acylation in itself.

DESCRIPTION OF THE PREFERRED EMBODIMENTS

Hitherto, the acylation of GPC supported on a higher fatty acid metallic salt with higher fatty acid anhydride has been carried out either in an organic solvent in the presence of basic catalyst or in the absence of catalyst in the absence of solvent. Its acylation in organic solvent in the absence of catalyst has never been reported up to today. This is for a reason that, in organic solvent, velocity of the reaction has been considered so low as impracticable unless a basic catalyst is used.

The present inventors have conducted many studies to search a more effective production process of DAPC. In course of the study, it was found that, if GPC supported on higher fatty acid metallic salt is acylated with a higher fatty acid anhydride in a specified organic solvent having active hydrogen atom on carbon atom and free from the risk of undergoing acylation in itself (or in a mixture comprising said specified organic solvent and other organic solvent), velocity of the reaction becomes higher unexpectedly, and the acylation progresses in a much shorter period of time than in the reaction in organic solvent in the presence of catalyst or in the reaction in the absence of solvent in the absence of catalyst to give the intended diacyl compound in a high yield and high quality. Based on this finding, this invention has been accomplished.

As the higher fatty acid anhydride represented by the formula: $(RCO)_2O$ used as an acylating agent, there can be used fatty acid anhydrides preferably having 10 to 24 carbon atoms such as straight- or branched-chain higher saturated fatty acid anhydrides, e.g., anhydrides of decanoic acid, lauric acid, myristic acid, palmitic acid, stearic acid, eicosanic acid, docosanoic acid, tetracosanic acid, 2-butyldodecanoic acid, 4-pentylundecanoic acid, etc.; and straight- or branched-chain higher unsaturated fatty acid anhydrides, e.g. anhydrides of oleic acid, linoleic acid, linolenic acid, 2-hexyl-2-decenoic acid, etc. These higher fatty acid anhydrides can be used in an amount of preferably about 2 to 5 moles per mole of GPC.

The GPC used in this invention as starting material is easily obtainable by hydrolyzing or alcoholyzing a natural lecithin such as yolk lecithin, soybean lecithin and the like. The lecithin thus obtained is supported on a higher fatty acid metallic salt in the usual way, i.e. according to the method mentioned in Japanese Pat. Publn. 62-9,599 = U.S. Pat. No. 4,690,784, Biochim. Biophys. Acta, 187, 520 (1969), etc.

As the higher fatty acid metallic salt, those having the same higher fatty acid residue as that of the higher fatty acid anhydride used as acylating agent are preferable. Usually, alkali metal salts and alkaline earth metal salts having such a higher fatty acid residue are preferably used.

Appropriate amount of said higher fatty acid metallic salt is usually about 2 moles per one mole of GPC.

It is indispensable in this invention that the carrier for supporting GPC is a higher fatty acid metallic salt. If other materials such as silica gel, alumina, diatomaceous earth and the like are used as the carrier, the reaction of this invention cannot progress satisfactorily.

Examples of the organic solvent having active hydrogen atom on carbon atom and free from the risk of undergoing acylation in itself used in this invention include alkanenitriles wherein the alkane moiety preferably has 1 to 5 carbon atoms, such as acetonitrile, propionitrile, butyronitrile, valeronitrile, hexanenitrile and the like; malonic diesters such as dimethyl malonate, diethyl malonate, dipropyl malonate, and the like; chloroform, and the like.

The organic solvent used in combination with said organic solvent having active hydrogen on carbon atom and free from the risk of undergoing acylation in itself may be any solvent, so far as it does not disturb the acylation of GPC and it is free from the risk of undergoing acylation in itself. Its examples include halogenated hydrocarbons such as methylchloroform, methylene chloride, ethylene chloride, carbon tetrachloride, and the like; aliphatic hydrocarbons preferably having 5 to 8 carbon atoms such as n-pentane, n-hexane, n-heptane, n-octane, cyclopentane, cyclohexane, cycloheptane, cyclooctane; aromatic hydrocarbons such as benzene, toluene, xylene, and the like; esters such as methyl acetate, ethyl acetate, propyl acetate, butyl acetate, methyl propionate, ethyl propionate, propyl propionate, and the like; ethers such as diethyl ether, diisopropyl ether, tetrahydrofuran and the like; dimethyl sulfoxide, dimethylformamide, and the like, though these solvents are not limitative. Although the amount of these reaction solvent is not critical, its appropriate amount is usually about 5 to 10 parts by volume, as total amount of solvent, per one part by weight of the supported GPC. The mixing ratio between the solvent having active hydrogen on carbon atom and free from the risk of undergoing acrylation in itself and said other organic solvent is usually 5-100 : 95-0, and the ratio should be appropriately selected in accordance with the adopted combination of solvents.

The temperature at which GPC supported on higher fatty acid metallic salt is acylated with higher fatty acid anhydride in a reaction solvent in the absence of catalyst is not critical, unless the effect of this invention is deteriorated. However, appropriate reaction temperature is usually about 40° to 100° C., preferably 50° to 90° C. In this case, appropriate reaction time is usually about 10 to 20 hours. The reaction is preferably carried out under a stream of inert gas such as nitrogen gas.

After the reaction, the product is after-treated in the usual way. If desired, it may be purified by column chromatography or the like arbitrarily. That is, after cooling the reaction mixture to deposit the higher fatty acid and higher fatty acid metallic salt from the reaction mixture and filtering off the deposited matter, the filtrate is purified by column chromatography to remove the excessive higher fatty acid anhydride and the small quantity of by-products (phosphate group-rearranged product, monoacyl product, etc.).

According to the process of this invention, the use of basic catalyst is unnecessary. Accordingly, the process of this invention is advantageous over processes using basic catalyst in the point of cost. Further, troublesome treatments for removing the basic catalyst such as a treatment using cation exchange resin and the like are unnecessary. Further, formation of byproducts such as phosphate group-rearranged product, monoacyl product, etc. is slight, which facilitates the after-treatment of the reaction.

Next, examples of this invention will be shown below. This invention is by no means limited by these examples.

Example 1 (Investigation of Reaction Solvent for Acylation. Part 1)

(1) Preparation of potassium palmitate-supported GPC

GPC in an amount of 25.7 g, 2000 ml of methanol, 52.2 g of palmitic acid and 11.4 g of potassium hydroxide were mixed to give a uniform solution at 40° C. and then concentrated to dryness to obtain 85.7 g of potassium palmitate-supported GPC.

(2) Acylation

To a mixture consisting of 8.57 g of the supported product obtained above (corresponding to 10 mmoles of GPC) and 18.4 g (1.86×Th) of palmitic anhydride was added 65 ml of solvent, and a reaction was carried out under a stream of nitrogen gas at 60° C. for 15 hours. After the reaction, methanol was added (this addition of methanol was unnecessary when the reaction solvent was chloroform), the insoluble matter was filtered off at 20° C., and the filtrate was concentrated to dryness to obtain crude dipalmitoyl-posphatidylcholine. It was subjected to silica gel column chromatography, and a fraction containing dipalmitoylphosphatidylcholine (hereinafter referred to as "DPPC") was taken out. It was concentrated to dryness to obtain the objective product. The results are summarized in Table 1.

TABLE 1

| Solvent | Yield of DDPC (%) | Quality of DPPC** |
|---|---|---|
| Chlorofom | 96.1 | TLC: nearly one spot |
| Carbon tetrachloride | 32.1 | Colored; lyso form contained |
| Dichloromethane* | 10.7 | TLC: nearly one spot |
| Ethylene chloride | 64.2 | " |
| Toluene | 62.3 | " |
| n-Hexane | 17.5 | Lyso form contained |
| Ethyl acetate | 50.6 | TLC: nearly one spot |
| Methyl ethyl ketone | 86.6 | Colored; lyso form contained |

TABLE 1-continued

| Solvent | Yield of DDPC (%) | Quality of DPPC** |
|---|---|---|
| Propionitrile | 88.2 | TLC: nearly one spot |

*Reaction temperature 38° C.
**For confirming the quality of product, TLC was carried out with the following developing solvent: Chloroform/Methanol/Water = 65/25/4 (by volume)

It is apparent from Table 1 that, when chloroform or propionitrile, having an active hydrogen atom on carbon atom and free from the risk of undergoing acylation in itself, is used as reaction solvent of acylation, yield and quality or product are very good. In contrast, in the case of methyl ethyl ketone which has an active hydrogen atom on carbon atom but is able to be acylated by itself, the product contains a large amount of lyso form (monoacyl derivative) and is colored, so that quality of the product is impractically bad, even though the yield is high. In all the cases of other solvents than methyl ethyl ketone, yield is unexceptionally low. Further, in cases of carbon tetrachloride and n-hexane, quality of product is not good.

Example 2 (Investigation of Reaction Solvent for Acylation. Part 2)

Potassium palmitate-supported GPC was prepared just in the same manner as in Example 1 (1). Using its 8.57 g (corresponding to 10 mmoles of GPC) as starting compound, acylation and after-treatment were carried out just in the same manner as in Example 1 (2) in a solvent mixture mentioned in Table 2 to prepared DPPC. The results are shown in Table 2.

TABLE 2

| Solvent | | Yield of DPPC (%) | Quality of DPPC |
|---|---|---|---|
| Ethyl acetate | 60 ml | 86.2 | TLC: nearly one spot |
| Acetonitrile | 5 ml | | |
| Carbon tetrachloride | 60 ml | 85.6 | TLC: nearly one spot |
| Acetonitrile | 5 ml | | |
| Ethylene chloride | 60 ml | 86.0 | TLC: nearly one spot |
| Acetonitrile | 5 ml | | |
| Toluene | 55 ml | 86.6 | TLC: nearly one spot |
| Chloroform | 10 ml | | |
| Ethylene chloride | 50 ml | 86.8 | TLC: nearly one spot |
| Propionitrile | 15 ml | | |

Table 2 demonstrates the following fact. Thus, even if a solvent is not good as a solvent for acylation when used alone in the points of yield and quality of product, it greatly improves yield and quality of product when used in combination with a solvent having active hydrogen atom on carbon atom such as acetonitrile, propionitrile, chloroform and the like.

Example 3

GPC in an amount of 5.14 g, 350 ml of methanol, 10.44 g of palmitic acid and 2.28 g of potassium hydroxide were mixed to give a uniform solution at 40° C. and then concentrated to dryness to obtain 17.14 g of potassium palmitate-supported GPC.

The potassium palmitate-supported GPC obtained above (17.14 g) was mixed with 35.6 g of palmitic anhydride and 60 ml of chloroform and reacted under reflux at 57° to 59° C. for 15 hours under a stream of nitrogen gas. After the reaction, the reaction mixture was cooled, the deposited palmitic acid and potassium palmitate were filtered off, and the filtrate was concentrated to obtain 35 g of a residue. It was purified by silica gel column chromatography to obtain purified DPPC in a yield of 13.8 g (94.0%).

mp 235° C.; $[\alpha]_D^{20} = +6.7°$ ($CHCl_3$, c=2.0);
TLC 1 spot; HPLC content 99.3%;
Fatty acid composition (GC): palmitic acid 99.4%.

Example 4

GPC in an amount of 5.14 g, 350 ml of methanol, 11.58 g of stearic acid and 1.63 g of sodium hydroxide were mixed to give a uniform solution at 50° C. and then concentrated to dryness to obtain 18.3 g of sodium stearate-supported GPC.

The sodium stearate-supported GPC obtained above (18.3 g) was mixed with 39.66 g of stearic anhydride and 120 ml of chloroform and reacted under reflux for 15 hours under a stream of nitrogen gas. After the reaction, the reaction mixture was cooled, the deposited stearic acid and sodium stearate were filtered off, the filtrate was concentrated to obtain 37 g of a residue, and it was subjected to silica gel column chromatography in the same manner as in Example 1 to obtain purified distearoyl-phosphatidylcholine in a yield of 14.5 g (91.8%).

mp 233° C.; $[\alpha]_D^{20} = +6.1°$ ($CHCl_3$, c=2.0);
TLC 1 spot; HPLC content 99.1%;
Fatty acid composition (GC): palmitic acid 99.1%.

Example 5

GPC in an amount of 5.14 g, 350 ml of methanol, 10.44 g of palmitic acid and 2.28 g of potassium hydroxide were mixed to give a uniform solution at 40° C. and then concentrated to dryness to obtain 17.14 g of potassium palmitate-supported GPC.

The potassium palmitate-supported GPC thus obtained (17.4 g) was mixed with 35.6 g of palmitic anhydride and 140 ml of propionitrile and reacted under reflux for 20 hours under a stream of nitrogen gas. After the reaction, the reaction mixture was cooled, the deposited palmitic acid and potassium palmitate were filtered off, the filtrate was concentrated to obtain 31 g of a residue, and it was subjected to silica gel column chromatography to obtain purified DPPC in a yield of 13.1 g (89.3%).

mp 235° C.; $[\alpha]_D° = +7.1°$ ($CHCl_3$, c=2.0);
TLC 1 spot; HPLC content 99.3%;
Fatty acid composition (GC): palmitic acid 99.5%.

This invention provides a novel process for producing diacyl-posphatidylcholines (DAPC). The marked effect of the process of the invention consists in that it is excellent in workability, gives DAPC of high purity in a high yield in a relatively short period of time and, since it uses no basic catalyst or the like, it requires no troublesome procedure for removing the catalysts, so that it can be commercialized easily.

What is claimed is:

1. A process for preparing a phosphatidylcholine compound of the formula

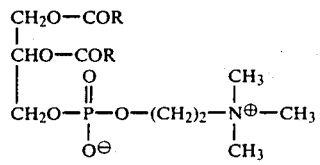

wherein R represents a saturated or unsaturated, straight or branched chain hydrocarbon residue, which comprises supporting glycero-phosphatidylcholine of the formula

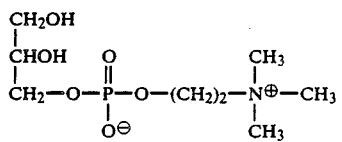

on a higher fatty acid metallic salt and acylating it with a higher fatty acid anhydride of the formula $(RCO)_2O$, wherein R is as defined above, in an organic solvent selected from the group consisting of an alkanenitrile, a malonic diester or chloroform, and in the absence of a catalyst.

2. A process according to claim 1, wherein the higher fatty acid anhydride has 10 to 24 carbon atoms.

3. A process according to claim 1, wherein the organic solvent is chloroform.

4. A process according to claim 1, wherein the said organic solvent may be combined with a halogenated hydrocarbon, an aliphatic hydrocarbon, an aromatic hydrocarbon, an ester, an ether, dimethyl sulfoxide or dimethylformamide.

5. A process according to claim 1, wherein the acylation is carried out at a temperature of 50° to 90° C.

* * * * *